United States Patent
Showalter et al.

(10) Patent No.: US 8,021,698 B2
(45) Date of Patent: Sep. 20, 2011

(54) METHOD OF IMPROVING CARDIOVASCULAR HEALTH

(75) Inventors: Holly Showalter, Waukee, IA (US); Zoraida DeFreitas, Polk City, IA (US); Luke Mortensen, Des Moines, IA (US)

(73) Assignee: Kemin Foods, L.C., Des Moines, IA (US)

( * ) Notice: Subject to any disclaimer, the term of this patent is extended or adjusted under 35 U.S.C. 154(b) by 0 days.

(21) Appl. No.: 11/961,685

(22) Filed: Dec. 20, 2007

(65) Prior Publication Data

US 2008/0233222 A1 Sep. 25, 2008

Related U.S. Application Data

(60) Provisional application No. 60/875,956, filed on Dec. 20, 2006.

(51) Int. Cl.
*A01N 65/00* (2009.01)
(52) U.S. Cl. ........................................ 424/725
(58) Field of Classification Search ........................ None
See application file for complete search history.

(56) References Cited

U.S. PATENT DOCUMENTS

| | | | |
|---|---|---|---|
| 2002/0172721 A1 * | 11/2002 | Boulos et al. | 424/646 |
| 2004/0022877 A1 * | 2/2004 | Green et al. | 424/736 |
| 2006/0088574 A1 | 4/2006 | Manning et al. | |

FOREIGN PATENT DOCUMENTS

CN 1107298 * 8/1995

OTHER PUBLICATIONS

USDA, 2 pages, 2009.*
Cardiovascular disease, 8 pages, 2010.*
John, J. H.; Ziebland, S.; Yudkin, P.; Roe, L. S.; Neil, H. A. W.; Effects of fruit and vegetable consumption on plasma antioxidant concentrations and blood pressure: a randomised controlled trial.; Lancet 359; 1969-74.; 2002.
Willeit, Johann; Bonvicini, Piero; D'Odorico, Anna; Egger, Georg; Kiechl, Stefan; Martines, Diego; Naccarato, Remo; Oberhollenzer, Friedrich; Sturniolo, Giacomo Carlo; High plasma levels of alpha- and beta-carotene are associated with a lower risk of atherosclerosis: Results from the Bruneck study. Atherosclerosis 153; 231-239; Nov. 2000.
Howard, A. N.; Williams, N. R.; Palmer, C. R.; Cambou, J. P.; Evans, A. E.; Foote, J. W.; Marques-Vidal, P.; McCrum, E. E.; Ruidavets, J. B.; Nigdikar, S. V.; Do hydroxy-carotenoids prevent coronary heart disease? A comparison between Belfast and Toulouse.; International journal for vitamin and nutrition research 66; 113-118.; 1996.
Sesso, Howard D.; Buring, Julie E.; Norkus, Edward P.; Gaziano, J. Michael; Plasma lycopene, other carotenoids, and retinol and the risk of cardiovascular disease in men; Am J Clin Nutr 81; 990-7.; May 5, 2005.
Romanchik, J. E.; Harrison, E. H.; Morel, D. W.; Addition of lutein, lycopene, or beta-carotene to LDL or serum in vitro: Effects on carotenoid distribution, LDL composition, and LDL oxidation.; Journal of Nutritional Biochemistry 8; 681-8.; 1997.
Brady, W. E.; Mares-Perlman, J. A.; Bowen, P.; Stacewicz-Sapuntzakis, M.; Human serum carotenoid concentrations are related to physiologic and lifestyle factors.; Journal of Nutrition 126; 129-37.; 1996.
Dwyer, J. H.; Paul-Labrador, M. J.; Fan, J.; Shircore, A. M.; Merz, C. N. B.; Dwyer, K. M.; Progression of carotid intima-media thickness and plasma antioxidants: the Los Angeles atherosclerosis study.; Arteriosclerosis, Thrombosis, and Vascular Biology 24; 313-19.; 2004.
Franke, A. A.; Harwood, P. J.; Shimamoto, T.; Lumeng, S.; Zhang, L-X.; Bertram, J. S.; Wilkens, L. R.; Marchand, L. L.; Cooney, R. V.; Effects of micronutrients and antioxidants on lipid peroxidation in human plasma and in cell culture.; Cancer Letters 79; 17-26.; 1994.
Zhang, C.; Williams, M. A.; Ware-Jauregui, S.; Sanchez, S.; Leisenring, W. M.; Laraburre, G.; King, I. B.; Bazul, V.; Plasma concentrations of carotenoids, retinol and tocopherols in preeclamptic and normotensive pregnant women.; American Journal of Epidemiology 151; S10.; Jun. 1, 2000.

* cited by examiner

*Primary Examiner* — Michael Meller
(74) *Attorney, Agent, or Firm* — Kent A. Herink; Emily E. Harris

(57) ABSTRACT

A nutritional supplement including β-cryptoxanthin is found to be effective at lowering blood pressure in mammals. β-cryptoxanthin therefore may be used to maintain cardiovascular health by lowering blood pressure, preventing high, elevated blood pressure and/or maintaining healthy blood pressure. Administration of β-cryptoxanthin in combination with safflower oil is particularly effective.

3 Claims, 4 Drawing Sheets

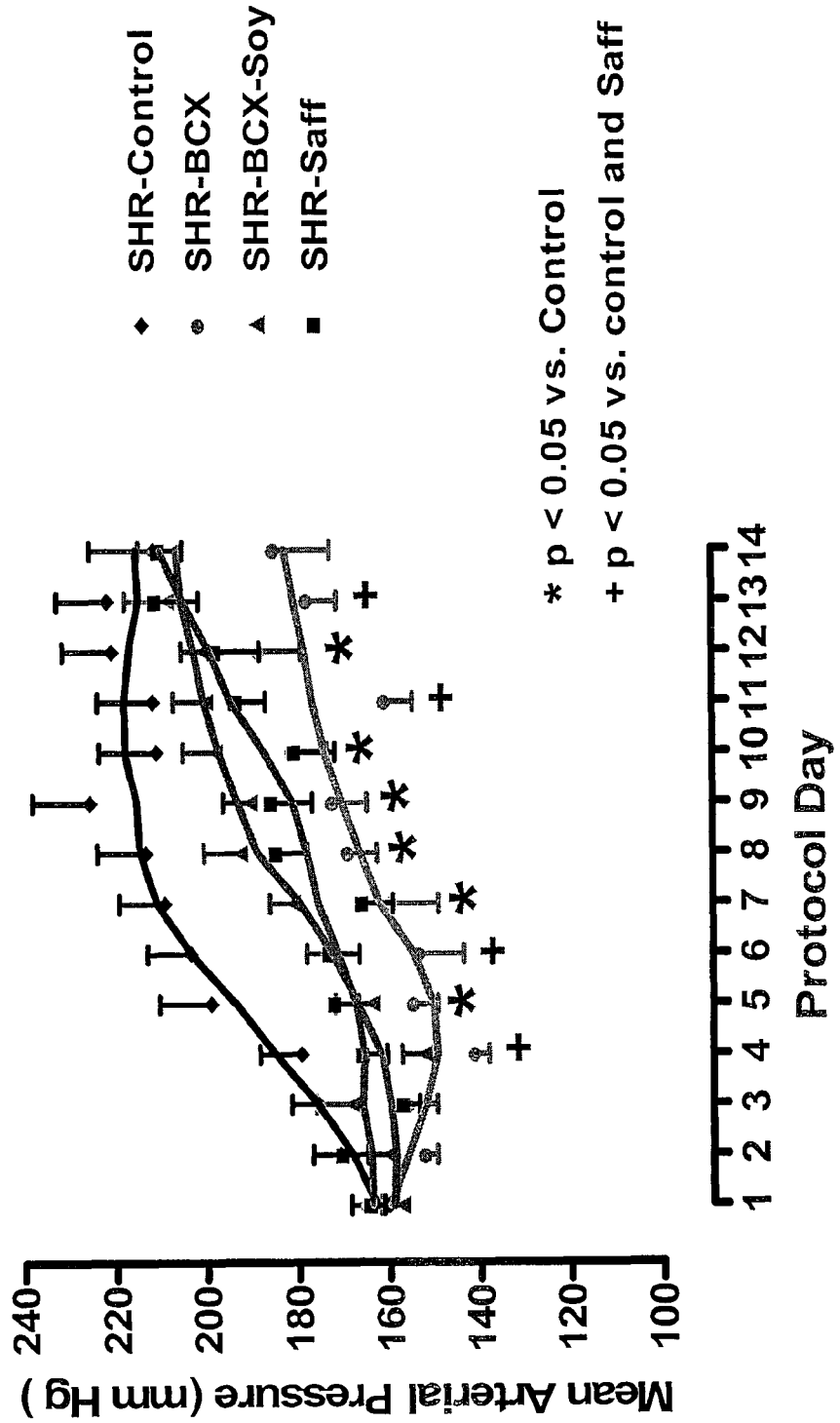
Fig. 1: Blood Pressure Response for Hypertensive (SHR) Rats

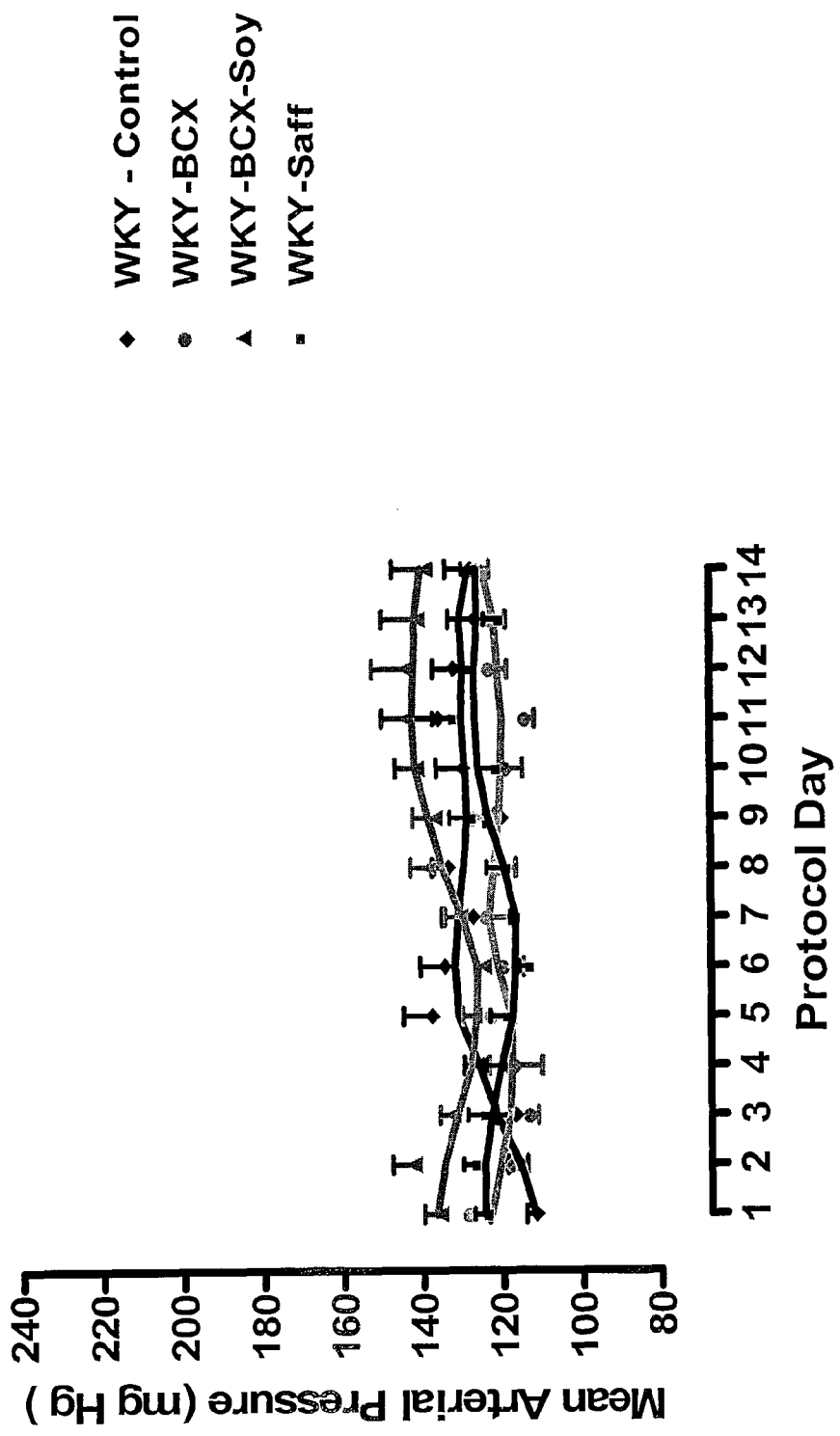
Fig. 2: Blood Pressure Response for Normal (WKY) Rats

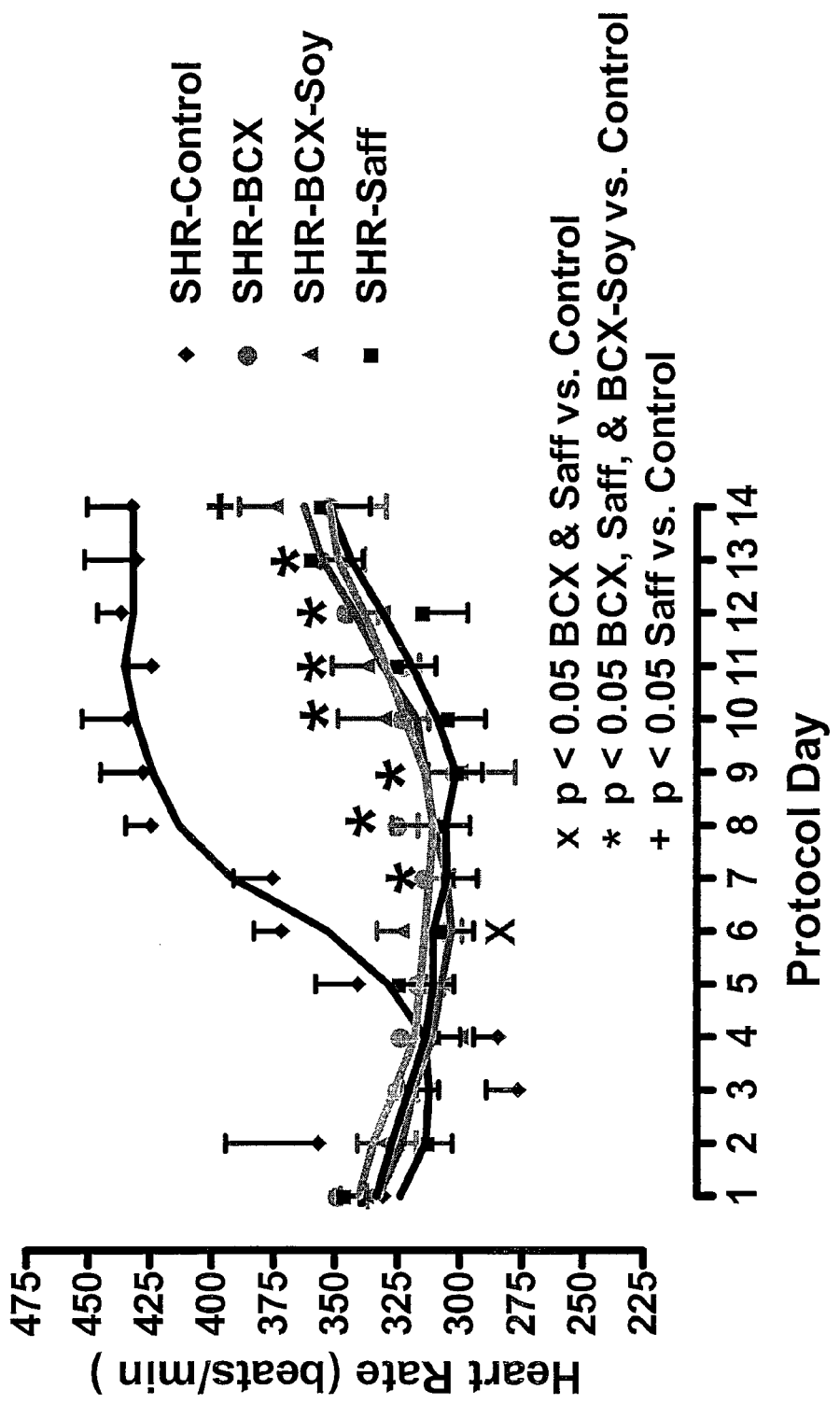
Fig. 3: Heart Rate Response for Hypertensive (SHR) Rats

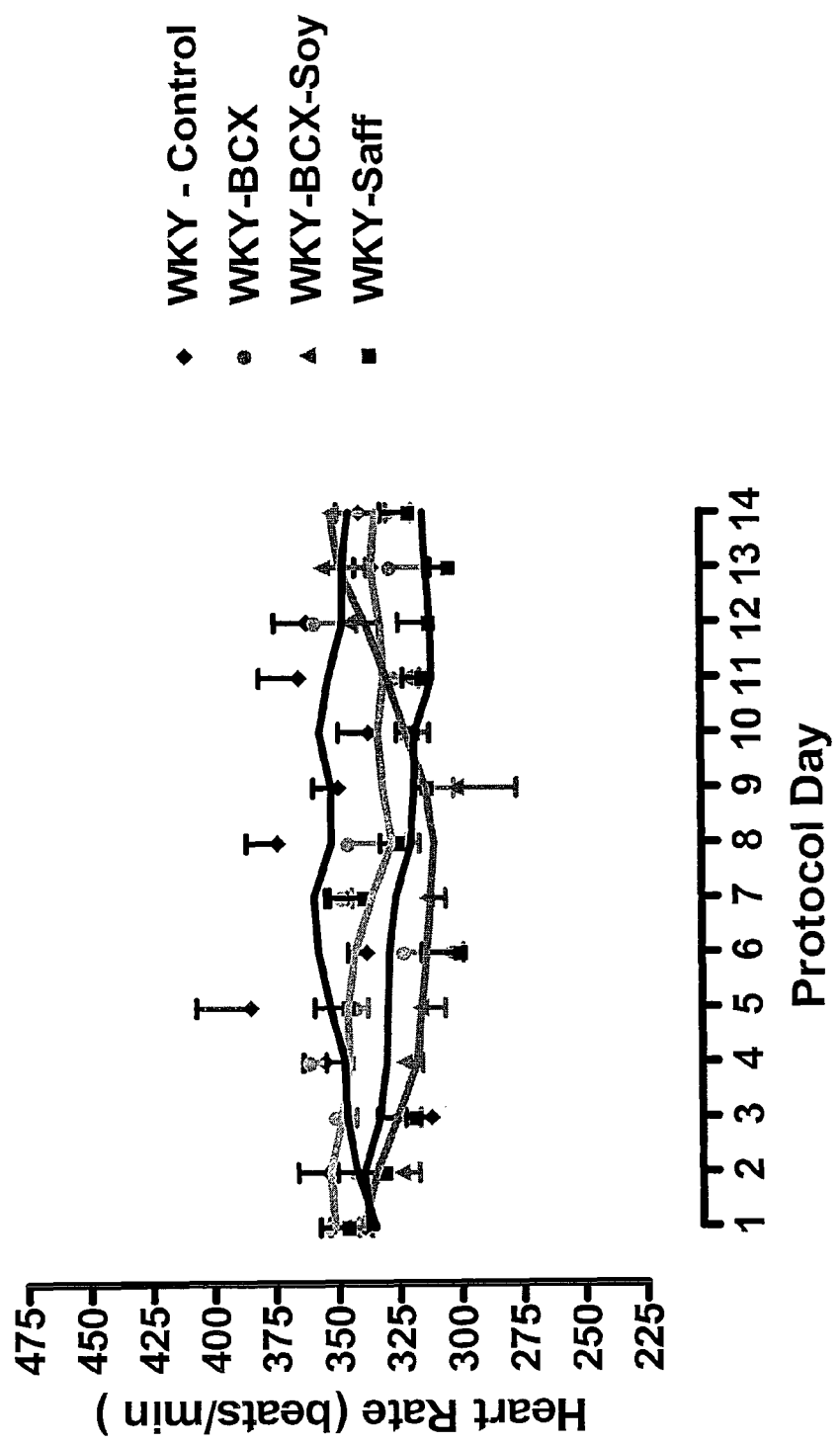
Fig. 4: Heart Rate Response for Normal (WKY) Rats

METHOD OF IMPROVING CARDIOVASCULAR HEALTH

This application claims priority to U.S. patent application Ser. No. 60/875,956 filed Dec. 20, 2006, which is incorporated herein in its entirety by this reference.

BACKGROUND OF THE INVENTION

The invention relates generally to methods of improving cardiovascular health and, more specifically, to the administration of β-cryptoxanthin to mammals in an effective dose to improve the cardiovascular health of the mammal.

Heart disease and stroke are the most common cardiovascular diseases. They are the first and third leading causes of death for both men and women in the United States, accounting for nearly 40% of all annual deaths. More than 910,000 Americans die of cardiovascular diseases each year. Although heart disease and stroke conditions are more common among people aged 65 or older, the number of sudden deaths from heart disease among people aged 15-34 has increased.

In addition, more than 70 million Americans currently live with a cardiovascular disease. Coronary heart disease is a leading cause of premature, permanent disability in the U.S. workforce. Stroke alone accounts for disability among about 1 million Americans. More than 6 million hospitalizations each year are because of cardiovascular diseases.

The economic impact of cardiovascular diseases on the nation's health care system continues to grow as the population ages. The cost of heart disease and stroke in the United States is projected to be $403 billion in 2006, including health care expenditures and lost productivity from death and disability.

There is a need, accordingly, for safe, efficacious and cost-effective treatments for preventing or ameliorating cardiovascular diseases and associated health implications.

SUMMARY OF THE INVENTION

The invention relates to the administration of β-cryptoxanthin to mammals, including humans, as a method of improving cardiovascular health. It has been demonstrated for the first time that the oral administration of β-cryptoxanthin reduces blood pressure in mammals and will lead to improved cardiovascular health.

BRIEF DESCRIPTION OF THE FIGURES

FIG. 1 is a chart of mean arterial pressure (MAP) for hypertensive (SHR) rats recorded daily over 14 days of dosing either β-cryptoxanthin in safflower oil (SHR-BCX), BCX combined with a soy extract in safflower oil (SHR-BCX-Soy), safflower oil only (SHR-Saff), or nothing (SHR-Control).

FIG. 2 is a chart of mean arterial pressure (MAP) for normal (WKY) rats recorded daily over 14 days of dosing either BCX in safflower oil (WKY-BCX), BCX combined with a soy extract in safflower oil (WKY-BCX-Soy), safflower oil only (WKY-Saff), or nothing (WKY-Control).

FIG. 3 is a chart of heart rate (HR) for hypertensive (SHR) rats recorded daily over 14 days of dosing either BCX in safflower oil (SHR-BCX), BCX combined with a soy extract in safflower oil (SHR-BCX-Soy), safflower oil only (SHR-Saff), or nothing (SHR-Control).

FIG. 4 is a chart of heart rate (HR) for normal (WKY) rats recorded daily over 14 days of dosing either BCX in safflower oil (WKY-BCX), BCX combined with a soy extract in safflower oil (WKY-BCX-Soy), safflower oil only (WKY-Saff), or nothing (WKY-Control).

DETAILED DESCRIPTION OF PREFERRED EMBODIMENTS

Human essential hypertension is characterized by impaired endothelium-dependent vasodilation, caused by oxidative stress. β-cryptoxanthin is demonstrated herein, for the first time, to have anti-hypertensive effects. In addition, β-cryptoxanthin is demonstrated to lower blood pressure and reduce heart rate, thereby exerting a cardiovascular protecting action.

In studies with spontaneously hypertensive rats (SHR), the applicants found that diets supplemented with β-cryptoxanthin lowered blood pressure and heart rate in SHR. Mean arterial pressure was significantly lower in SHR fed β-cryptoxanthin, compared with a control group fed food only as well as a control group fed a diet supplemented with safflower oil ($P<0.05$) (FIG. 1). The heart rate response was significantly lower for SHR fed β-cryptoxanthin, compared to a control group fed food only ($P<0.05$) (FIG. 3). A diet supplemented with β-cryptoxanthin combined with a soy extract also showed significant results in lowering the heart rate response in SHR (FIG. 3).

It will be appreciated by those skilled in the art that β-cryptoxanthin may be administered to a subject by a variety of routes, including oral administration, or injection. The amount of β-cryptoxanthin to be administered will vary widely depending upon the subject and the nature and extent of the condition for which the β-cryptoxanthin is being administered. Typically, β-cryptoxanthin is formulated as a composition which may be administered intravenously or by oral ingestion. The composition may be ingested or intravenously administered in any dosage levels and dosage frequencies suitable for lowering blood pressure and/or lowering heart rate response.

The composition of the invention may also be a food product, including, but not limited to, a nutritional supplement. The composition may be formulated into solid or liquid preparations, for example tablets, capsules, powders, solutions, suspensions and dispersions. Liquid forms include carriers such as water and ethanol, with or without other agents such as pharmaceutically acceptable surfactants or suspending agents.

Compositions of the present invention may include β-cryptoxanthin in an amount between 0.03 mg and about 20 mg, preferably between 0.05 mg and about 6 mg, and more preferably between 0.3 and 3 mg. The compositions are administered to humans to provide β-cryptoxanthin in an amount between 0.1 mg per day and 20 mg per day, preferably between 0.15 mg per day and 6 mg per day, and more preferably between 0.8 mg per day and 3 mg per day. The compositions may include extracts of soy, including but not limited to soy isoflavone extracts, in an amount between 0.3 mg and about 250 mg, preferably between 1.3 mg and about 200 mg, and more preferably between 6 and 150 mg. The compositions are administered to humans to provide extracts of soy in an amount between 1 mg per day and 250 mg per day, preferably between 5 mg per day and 200 mg per day, and more preferably between 20 mg per day and 150 mg per day. The compositions may also include safflower oil in an amount when administered comprises between 10 mg/kg of body weight and 3 g/kg of body weight, preferably between 20 mg/kg of body weight and 500 mg/kg of body weight, and more preferably between 50 mg/kg of body weight and 300 mg/kg of body weight.

EXAMPLE 1

In this example, the cardiovascular effects of β-cryptoxanthin (BCX) in chronically-instrumented, conscious rats is demonstrated. The example shows the protective role of BCX in the maintenance of hypertension in genetically hypertensive animals. Additionally, daily soy isoflavone (SoyLife®, Acatris, Minneapolis, Minn.) supplementation was administered with BCX to both normotensive (WKY) and spontaneously hypertensive (SHR) rats to determine any beneficial hemodynamic contributions of soy to genetic hypertension. Animals receiving daily oral doses of BCX or BCX combined with the soy extract and comparisons of specific hemodynamic parameters (heart rate and blood pressure) were monitored for a period of two weeks in SHR rats and their genetically WKY counterparts. Plasma hydrogen peroxide concentrations were evaluated and show the effects of BCX on reactive oxygen species and their purported contribution to elevations in blood pressure in this hypertensive animal paradigm (Wilcox C. S., Reactive oxygen species: roles in blood pressure and kidney function. Curr Hypertens Rep. 2002 April;4(2):160-6).

The example used 36 WKY rats and 36 SHR rats assigned to the protocols set out in Table 1.

TABLE 1

Animals and Treatments

| treatment | WKY (male) | SHR (male) |
|---|---|---|
| BCX | N = 8 | N = 8 |
| BCX + soy | N = 8 | N = 8 |
| Oil Controls | N = 8 | N = 8 |
| Controls | N = 8 | N = 8 |
| Baseline BCX | N = 4 | N = 4 |

The animals (n=64) of the first 4 rows of Table 1 in this study underwent the following surgical procedure:

1. Three days prior to the beginning of experiments, femoral arterial and venous catheters were implanted for the measurement of blood pressure and heart rate and for the collection of blood samples for the analysis of plasma CRP and cholesterol. Animals were housed in metabolic cages for chronic daily analysis for the remainder of the protocol.

2. The animals (n=4) of the Baseline BCX row of Table 1 underwent the following procedure:

At one day prior to beginning of protocol, blood samples were obtained from 4 SHR rats and 4 WKY animals to serve as a baseline BCX benchmark. Baseline BCX cannot be obtained from the other rats due to the volume of blood needed for analysis. These animals were sacrificed for their blood sample and were not placed on any BCX or isoflavone feed. This measurement provided a baseline measurement of BCX in the plasma from their diets prior to arriving at DMU. The other 64 animals had pooled samples taken for baseline CRP, cholesterol, and plasma hydrogen peroxide. Table 1 shows the breakdown of animals and treatment groups.

General Surgical Preparation and Methodology:

General care: SHR and WKY rats (Harlan, Indianapolis, Ind.) at age 10 weeks and weighing ~250g were used as experimental subjects and monitored for a two week period. All experimental protocols were performed in conscious, unrestrained animals. The animals were individually housed in wire mesh cages in temperature-controlled rooms (23° C.) with a 12-hour light/dark cycle. Each animal was allowed free access to isoflavone reduced chow (Harlan, Indianapolis, Ind.) and distilled water throughout the protocol(s). In addition to ad libitum food and water, animals were dosed daily by oral gavage with BCX (1.0 mg/kg, in safflower oil) or BCX +soy (1.0 mg BCX/kg+80 mg isoflavones/kg, in safflower oil). BCX dosage levels were based on the amount of BCX humans consume when eating according to the Dietary Guidelines for Americans: 0.5-1.0 mg per day (United States Department of Health and Human Services and United States Department of Agriculture. Dietary Guidelines for Americans 2005. Jan. 12, 2005. http://www.healthierus.gov/dietaryguidelines/; Centers for Disease Control and Prevention. National Center for Health Statistics. National Health and Nutrition Examination Survey Data 2001-2002. http://www.cdc.gov/nchs/about/major/nhanes/nhanes01-02.htm).

Dietary intake of 80 mg isoflavones per day has been shown to reduce systolic and diastolic blood pressure among highrisk, middle-aged men (Sagara, M., Kanda, T., Jelekera, M., Birt, T., Birt, C., Yamori, Y. Effects of Dietary Intake of Soy Protein and Isoflavones on Cardiovascular Disease Risk Factors in High Risk, Middle-Aged Men in Scotland, J Amer Col of Nutr, 2003; 23(1): 85-91).

SHR rats: SHR rats are normotensive at birth (compared to their WKY counterparts) and begin to demonstrate hypertension at ~5 weeks of age. After this time, mean arterial pressure (MAP) increases dramatically and maximizes to approximately $171 \pm 2.0$ mmHg in adults animals (Yamori Y, Horie R, Nara Y, Kihara M, Ikeda K, Mano M, Fujiwara K. Dietary prevention of hypertension in animal models and its applicability to human. Ann Clin Res. 1984;16 Suppl 43:28-31).

Catheterization: All surgical procedures were performed in animals anesthetized with sodium pentobarbital (Nembutal®, Abbott Laboratories) at a dose of 50 mg/kg, i.p. In addition, all surgery was performed under sterile conditions in a location in the laboratory dedicated for that purpose and according to those procedures adopted by the IACUC at Des Moines University-Osteopathic Medical Center. The implantations of femoral arterial and venous catheters were performed three days prior to any experimentation. The arterial and venous catheters were constructed from silicone and Tygon® tubing (Saint-Gobain Performance Plastics Corporation). The smaller silicone tubing was placed within the vessel, via the external iliac artery, to minimize tissue irritation and reaction. Normal body temperature was maintained during anesthesia via an electronically maintained dermal pad. The animals were shaved at the top of the head, back of the neck and the inner left leg. The silicone tips were inserted through a 3.0 cm incision made on the inner left leg for cannulation of the internal iliac vein and femoral artery; the arterial catheter was sutured to the leg in a manner preventing occlusion of the catheter during normal rat movement. Excess catheter was directed subcutaneously and externalized through a 2.5 cm incision made in the dermis overlying bregma. The cranial incision was made with a scalpel after which three 0.19" jeweler's screws were attached to the cranium in a 1.0 $cm^2$ area which encompasses bregma. After externalization, the catheters were threaded through a metal spring tether. The spring tethers were permanently attached to the skull with dental acrylic adhesive using the attached machine screws as cranial anchors. The animal was then administered penicillin G, 20,000 U, i.m., allowed to regain consciousness on the heated pad and placed in a metabolic cage. When not in use, the catheters were kept patent by filling with a heparinized (1000 U/ml) sucrose solution.

Beta-Cryptoxanthin and Soy Isoflavone Materials:

Beta-cryptoxanthin was purified using the following HPLC method. Crude BCX dry cake was prepared following the procedures outlined in U.S. patent application Ser. No. 10/973,204, filed Oct. 26, 2004, which is incorporated herein by this reference. A mobile phase is prepared by mixing 3.6 L HPLC grade methanol and 0.4 L HPLC grade methyl tert-butyl ether (MTBE). On-half gram of BCX dry cake is weighed into an amber flask to which is added 10 ml of methylene chloride and 90 ml of the mobile phase. The mixture is stirred for 10 min and the filtered through a 0.45 micron PTFE filter to generate the BCX injection solution. The HPLC is fitted with a Waters YMC carotenoid column (C30; 250 mm×20; mm; 5 micron particles) and 20 ml of injection solution is injected (20 ml/min flow rate; 40 min run time; 452 nm). When the BCX peak appears (approximate retention time is 24.8 min), the eluent is diverted to an amber flask until all the BCX has eluted (approximately 28 min). The collected eluent is cooled at −20° C. for several hours to form crystals of BCX. If crystals fail to form, the eluent may be concentrated with a rotary evaporator (40° C. water bath) until crystals form, and then the solution is cooled, preferably for several hours. The crystals are collected by filtration via a Kontes Ultraware 90 nm microfiltration assembly (Kontes Asset Management) or equivalent with a Durapore® (Millipore Corporaton) membrane filter (0.45 μm HVHP04700). The crystals may be dried in a desiccator under high vacuum.

Soy isoflavones 40% extract (SoyLife®) were purchased from Acatris. The pure BCX standard and soy isoflavones (Lot# 63D/1737/4) were formulated with certified organic deodorized high oleic safflower oil (Spruce Foods Lot#91726) as shown below in Table 2.

TABLE 2

BCX and BCX/Soy in Safflower Oil Formulations

First BCX/Safflower oil mix

| BCX Lot # | TC* % | BCX % |
|---|---|---|
| BCX053105RA | 98.6 | 97.1 |

BCX Concentration in oil: 0.504 mg/ml
Safflower oil lot #: 91726

Second BCX/Safflower oil mix
Three lot #'s BCX mixed in oil

| BCX Lot # | TC* % | BCX % |
|---|---|---|
| BCX053105RA | 98.6 | 97.1 |
| BCX062905 | 100.8 | 95.2 |
| BCX070105 | 98.7 | 98.1 |
| Average | 99.4 | 96.8 |

BCX Concentration in oil: 0.522 mg/ml
Isoflavone: 40 mg/ml
Safflower oil: 143 ml
Lot # KH85-72-1

*TC = total carotenoids

Hemodynamic Data Acquisition (MAP and HR): On a daily basis, mean arterial pressure was measured directly through a catheter implanted in the femoral artery of each animal. The catheter was attached to a Cobe7 pressure transducer (Model 41-500) coupled to a MacLab® Transbridge amplifier (ADInstruments, Australia). Heart rate was measured with software triggered by the arterial pressure pulse. Analog signals were digitized using a MacLab® A/D converter system and a Macintosh® computer (Apple Computer, Inc.). The data was acquired at a rate of 0.1 Hz. Data was collected over a period of 10-15 minutes each day. Data analysis was performed using multifactorial ANOVA (SigmaStat®, Jandel Corporation) for group comparisons. Significant differences ($p<0.05$) were evaluated using post hoc t-test. The results are displayed in FIGS. 1-4.

Blood Pressure Results

Eight rats from each test group (SHR-BCX, SHR-BCX-Soy, WKY-BCX, and WKY-BCX-Soy) and control groups (SHR-Control, SHR-Saff, WKY-Control, and WKY-Saff) have been run using this protocol and the blood pressure means of each day are graphically displayed for the SHR rats in FIG. 1 and for the WKY rats in FIG. 2. Designations of * and + on FIG. 1 indicate statistical differences on the particular day between the groups identified in the legend. Days 4-13 showed there to be a statistically significant difference between the SHR1 controls and the SHR/BCX group. On days 4, 6, 11, and 13, there was a significant difference between the SHR-Saff oil controls and SHR-BCX. The WKY normotensive rats did not show any change in blood pressure over the 14 days vs. any of the treatments.

Statistical analysis was performed using the mean blood pressure data over the entire 14-day experiment and the data are shown in Table 3. The SHR-BCX, SHR-BCX-Soy, and SHR-Saff safflower oil controls all statistically decreased the blood pressure vs. the SHR-Control (rat chow only). The P value comparing SHR-BCX to SHR-Saff was 0.063 over the entire 14 day period, although there were individual days with statistical significance (FIG. 1). The SHR-BCX-Soy combination did not statistically affect the blood pressure vs. the SHR-Saff safflower oil controls. The WKY (normotensive rats) did not show any significant blood pressure change after supplementation with BCX, BCX-Soy, or safflower oil itself (Table 3).

TABLE 3

Blood Pressure Student-Neuman-Keuls Post Hoc Test
(All pairwise multiple comparison procedure)

| Comparison over 14 days | P value | Significance |
|---|---|---|
| SHR-Control vs. SHR-BCX | <0.001 | Yes |
| SHR-Control vs. SHR-Saff | 0.021 | Yes |
| SHR-Control vs. SHR-BCX-Soy | 0.011 | Yes |
| SHR-BCX-Soy vs. SHR-BCX | 0.083 | No |
| SHR-BCX-Soy vs. SHR-Saff | 0.830 | No |
| SHR-Saff vs. SHR-BCX | 0.063 | No |
| WKY-BCX-Soy vs. WKY-BCX | 0.206 | No |
| WKY-BCX-Soy vs. WKY-Control | 0.228 | No |
| WKY-BCX-Soy vs. WKY-Saff | 0.177 | No |
| WKY-Saff vs. WKY-BCX | 0.699 | No |
| WKY-Saff vs. WKY-Control | 0.570 | No |
| WKY-Control vs. WKY-BCX | 0.648 | No |

Heart Rate Results

Eight rats from each test group (SHR-BCX, SHR-BCX-Soy, WKY-BCX, and WKY-BCX-Soy) and control groups (SHR-Control, SHR-Saff, WKY-Control, and WKY-Saff) have been run using this protocol and the heart rate means of each day for the SHR rats are graphically displayed in FIG. 3 and for the WKY rats in FIG. 4. Designations of * and +on FIG. 3 indicate statistical differences on the particular day between the groups identified in the legend. Days 6-13 showed there to be a statistically significant lower heart rate in the SHR-BCX vs. the SHR-Control. Days 6-14 showed that the SHR-Saff oil control group had a statistically significant decrease in heart rate vs. the SHR-Control. Days 7-13 showed there to be a statistically significant lower heart rate in the SHR-BCX-soy vs. the SHR-Control.

Statistical analysis was performed using the mean heart rate data over the entire 14-day experiment and the data are shown in Table 4. The SHR-BCX, SHR-BCX-Soy, and SHR-Saff safflower oil controls all statistically decreased the heart rate vs. the SHR-Control (rat chow only). There was no statistical difference between the heart rate of the SHR-BCX and SHR-BCX-Soy groups (P=0.791). There was also no statistical difference between the SHR-Saff oil control heart rate and the SHR-BCX (P=0.964) and SHR-BCX-Soy (P=0.968). There was a statistical decrease in heart rate between the WKY-Control and both the WKY-Saff oil controls (P=0.010) and the WKY-BCX (P=0.018) groups. There was a statistical increase in heart rate in the WKY-BCX-Soy fed rats vs. the WKY-Saff safflower oil controls. There was no statistical difference in the other WKY test group combinations (Table 4).

TABLE 4

Heart Rate Student-Neuman-Keuls Post Hoc Test
(All pairwise multiple comparison procedure)

| Comparison over 14 days | P value | Significance |
|---|---|---|
| SHR-Control vs. SHR-BCX | <0.001 | Yes |
| SHR-Control vs. SHR-Saff | <0.001 | Yes |
| SHR-Control vs. SHR-BCX-Soy | <0.001 | Yes |
| SHR-BCX vs. SHR-BCX-Soy | 0.791 | No |
| SHR-BCX-Soy vs. SHR-Saff | 0.968 | No |
| SHR-BCX vs. SHR-Saff | 0.964 | No |
| WKY-BCX-Soy vs. WKY-BCX | 0.396 | No |
| WKY-Control vs. WKY-BCX-Soy | 0.953 | No |
| WKY-BCX-Soy vs. WKY-Saff | 0.011 | Yes |
| WKY-BCX vs. WKY-Saff | 0.539 | No |
| WKY-Control vs. WKY-Saff | 0.010 | Yes |
| WKY-Control vs. WKY-BCX | 0.018 | Yes |

The foregoing description and drawings comprise illustrative embodiments of the present inventions. The foregoing embodiments and the methods described herein may vary based on the ability, experience, and preference of those skilled in the art. Merely listing the steps of the method in a certain order does not constitute any limitation on the order of the steps of the method. The foregoing description and drawings merely explain and illustrate the invention, and the invention is not limited thereto, except insofar as the claims are so limited. Those skilled in the art who have the disclosure before them will be able to make modifications and variations therein without departing from the scope of the invention.

We claim:

1. A method of reducing high blood pressure in a mammal in need thereof, comprising the step of administering to the mammal a nutritional supplement consisting essentially of purified β-cryptoxanthin in an amount between 0.1 mg and 20 mg per day.

2. A method as defined in claim 1, wherein the amount of β-cryptoxanthin is between 0.15 mg and 6 mg per day.

3. A method as defined in claim 1, wherein the amount of β-cryptoxanthin is between 0.8 mg and 3 mg day.

* * * * *